US012721753B2

(12) United States Patent
Palko et al.

(10) Patent No.: US 12,721,753 B2
(45) Date of Patent: Sep. 1, 2026

(54) SINGLE-HANDED ELECTROSURGICAL DEVICE AND METHODS THEREOF

(71) Applicant: West Virginia University Board of Governors on Behalf of West Virginia University, Morgantown, WV (US)

(72) Inventors: Joel Palko, Morgantown, WV (US); Ali Rai, Morgantown, WV (US); Maryam Budaris, Morgantown, WV (US); Justin Robinson, Morgantown, WV (US); Dakota Sanders, Fairmont, WV (US); Sarah Westfall, Hurricane, WV (US)

(73) Assignee: WEST VIRGINIA UNIVERSITY BOARD OF GOVERNORS ON BEHALF OF WEST VIRGINIA UNIVERSITY, Morgantown, WV (US)

( * ) Notice: Subject to any disclaimer, the term of this patent is extended or adjusted under 35 U.S.C. 154(b) by 576 days.

(21) Appl. No.: 18/139,903

(22) Filed: Apr. 26, 2023

(65) Prior Publication Data

US 2024/0074898 A1 Mar. 7, 2024

Related U.S. Application Data

(60) Provisional application No. 63/335,206, filed on Apr. 26, 2022.

(51) Int. Cl.
*A61B 17/04* (2006.01)
*A61B 18/08* (2006.01)
(Continued)

(52) U.S. Cl.
CPC *A61F 9/00781* (2013.01); *A61B 2017/00424* (2013.01); *A61B 17/0467* (2013.01);
(Continued)

(58) Field of Classification Search
CPC .. A61B 2018/00595; A61B 2018/1407; A61B 2018/141; A61B 17/8869;
(Continued)

(56) References Cited

U.S. PATENT DOCUMENTS 6,106,545 A 8/2000 Egan
8,529,589 B2 9/2013 Cartledge et al.
(Continued)

OTHER PUBLICATIONS

Ninomiya, H., & Inomata, T. (2006); "Microvascular anatomy of the pig eye: scanning electron microscopy of vascular corrosion casts." The Journal of veterinary medical science 68(11) Jul. 2006.
(Continued)

*Primary Examiner* — Majid Jamialahmadi
(74) *Attorney, Agent, or Firm* — Thomas | Horstemeyer, LLP

(57) ABSTRACT

Various examples are provided related to electrosurgical devices which can be used during ab interno canaloplasty or pupilloplasty surgery. In one example, a suture tensioning and electrocautery device includes a casing; suture grips protruding out of a proximal end of the casing; a suture tensioning and retracting system connected to the suture grips; and a suture electrocautery system. In another example, a method includes affixing ends of a suture to respective suture grips protruding out of a proximal end of a suture tensioning and electrocautery device; tying the ends of the suture and tensioning the suture by rotating the suture grips to dilate Schlemm's canal; and heating the tied ends of the suture to maintain the tensioning of the suture thereby sustaining dilation of the Schlemm's canal.

19 Claims, 9 Drawing Sheets

(51) Int. Cl.
*A61F 9/007* (2006.01)
*A61B 17/00* (2006.01)
*A61B 18/00* (2006.01)

(52) U.S. Cl.
CPC ... *A61B 17/0469* (2013.01); *A61B 2017/0496* (2013.01); *A61B 2018/00101* (2013.01); *A61B 18/082* (2013.01)

(58) Field of Classification Search
CPC .......... A61B 17/0469; A61B 17/32056; A61B 17/221; A61B 2017/0496; A61B 2017/2212; A61B 2017/2215; A61B 2017/2217
See application file for complete search history.

(56) References Cited

U.S. PATENT DOCUMENTS

| | | | | |
|---|---|---|---|---|
| 9,700,363 | B2 | 7/2017 | Jaramillo et al. | |
| 10,405,847 | B2 | 9/2019 | Petry et al. | |
| 10,568,676 | B2 | 2/2020 | Wade | |
| 2005/0228403 | A1* | 10/2005 | Ho .................. | A61B 17/32056 606/113 |

OTHER PUBLICATIONS

Tsai, J. "High eye pressure and glaucoma. Glaucoma Research Foundation". Retrieved Sep. 21, 2021.

Llobet, A., Gasull, X., & Gual, A. (Oct. 2003). "Understanding Trabecular Meshwork Physiology: A Key to the Control of Intraocular Pressure". American Physiological Society, 18(5).

Wang, K. (May 2018); "Mechanical Properties of Trabecular Meshwork", A dissertation presented to The Academic Faculty.

Vold, S. (Apr. 2021). "Canaloplasty and Trabeculotomy with the OMNI System in Pseudophakic Patients with Open-Angle Glaucoma: The ROMEO Study." American Academy of Ophthalmology.

* cited by examiner 100
109
118
127
124
112

100
109
109
118
127
130
112

SINGLE-HANDED ELECTROSURGICAL DEVICE AND METHODS THEREOF

CROSS REFERENCE TO RELATED APPLICATIONS

This application claims priority to, and the benefit of, U.S. provisional application entitled "Single-Handed Electrosurgical Device to Manipulate Suture Tension to Reduce Intraocular Pressure and Methods Thereof" having Ser. No. 63/335,206, filed Apr. 26, 2022, which is hereby incorporated by reference in its entirety.

BACKGROUND

Glaucoma is an ailment of the eye that is believed to be caused by insufficient channel drainage along Schlemm's canal leading to an increased intraocular pressure (IOP), which then leads to damage to the optic nerve. Current methods to treat glaucoma include many surgeries that remove ocular tissues. These invasive surgeries allow for greater canal opening, but also produce scar tissue that can cause complications for the patient later in life, typically resulting in follow-up surgeries. Less invasive surgeries may avoid this issue of scarring but are generally less effective as they typically open only a portion of the canal (e.g., 90 degrees of the full 360 canal). There is a need for a less invasive approach such as ab interno canaloplasty that is more effective by allowing the whole canal to open, while remaining less abrasive than standard invasive procedures.

SUMMARY

Aspects of the present disclosure are related to electrosurgical devices which can be used during ab interno canaloplasty or pupilloplasty surgery. A limitation of these surgical procedures includes the need to create a knot ab externo, to pull the knot into the eye, and to control the tension being applied to the suture during the operation, which is both time consuming and difficult. Currently, sutures must be externalized via additional cuts in the cornea, then tied together using modifications of a Siepser knot, with the knot then having to be pulled back into the eye. This current standard technique is time consuming, requires several additional paracenteses to the eye, and is technically challenging to perform.

The ability to suture within the eye is less invasive, less time consuming, and safer for the subject. In one aspect, among others, a single-handed electrosurgical device can set and maintain suture tension during the ab interno canaloplasty or pupilloplasty surgery. A suture can first be passed through the canal via an incision into the eye. The electrosurgical device can twist the ends of the suture together and then perform thermal cautery at the suture connection by exposing it to a heating element to set and maintain the tension of the overall suture without melting through the suture entirely. The device can then release the suture, allowing it to be withdrawn. The single-handed electrosurgical device can provide a faster, simpler, safer, and less invasive way to perform ab interno canaloplasty and pupilloplasty. This device also allows for more of these types of eye surgeries to occur as less surgical training is needed to use the device and less time is needed in the operating room.

The current Minimally Invasive Glaucoma Surgery (MIGS) market is large and has grown exponentially over the last decade. Commercial products can include the handheld electrosurgical device as well as sutures compatible with the device. The design of electro and thermal cautery clamps or mechanisms within the device can perform at ideal temperatures for suture manipulation rather than outside or at extreme heats in which they exist for current alternative applications. The braiding and knotting mechanism for sutures on the micro-scale can utilize machine mechanics within the device that enable tension control and preservation, rather than human control of the sutures directly. This device offers unique advantages to suturing within the eye and is applicable to glaucoma surgery and anterior segment reconstructive surgery as nonlimiting examples. This device can allow for permanent 360 degree expansion of the Schemm's canal, while current competing devices only allow for about 90 degree expansion.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
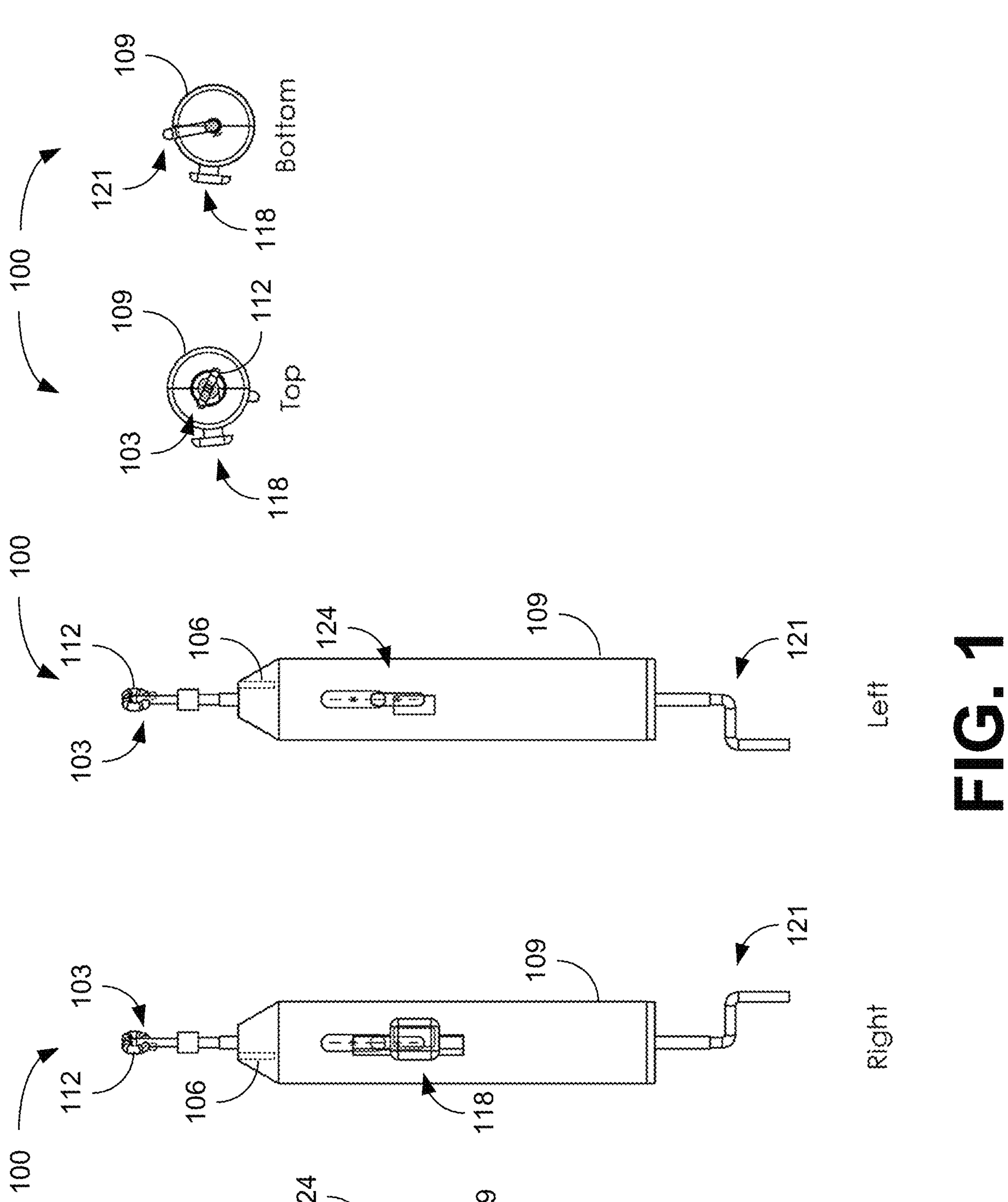
FIG. 1 illustrates an example of an electrosurgical device that can be used for suture tensioning and electrocautery, in accordance with various embodiments of the present disclosure.

Disclosed herein are various examples related to electrosurgical devices which can be used during ab interno canaloplasty or pupilloplasty surgery. For example, an electrosurgical device can be used in glaucoma surgery (e.g., ab interno canaloplasty) that would allow a surgeon to set the tension of a suture that is passed through Schlemm's canal, as well as ligate the ends of the suture together using electrocautery. The electrosurgical device can be single-handed to facilitate use by the surgeon (e.g., for safety, use with a gonioprism, comfort and/or ease of use). Reference will now be made in detail to the description of the embodiments as illustrated in the drawings, wherein like reference numbers indicate like parts throughout the several views.

Referring to FIG. 1, shown are various views of an example of an electrosurgical device 100 that can be used for suture tensioning and electrocautery. In a nonlimiting example, the electrosurgical device 100 can be a single-handed device configured to perform ab interno canaloplasty in a way that allows for the suture tension to be set and maintained using a tensioning system 103 and a suture electrocautery system 106 including a heating element. The suture electrocautery system 106 can be configured to allow the suture ends to be electrocauterized while under tension. A casing 109 can cover or enclose at least a portion of the tensioning system 103 and the suture electrocautery system 106. A power source can be included in or attached to the casing 109. This configuration can allow the surgeon to control not only the tension of the suture, but also join the suture ends together, all within one device.

In a nonlimiting example, a suture can be passed through an incision in the Schlemm's canal using a syringe-like delivery vehicle, and then fed through the Schlemm's canal until it emerges from the opposing side of the incision. Suture tensioning can then be accomplished by attaching the two ends of the suture to the tensioning system 103 of the electrosurgical device. As shown in FIG. 1, the tensioning system 103 extends from a proximal end of the device to facilitate attachment and tensioning of the suture. The tensioning system 103 can comprise grips 112 attached to an end of a rod or shaft extending through the casing 109. For example, the tensioning system 103 can include two respective grips 112 protruding or extending from the proximal end. The grips 112 grasp the ends of the suture for tensioning.

Figure 2A:
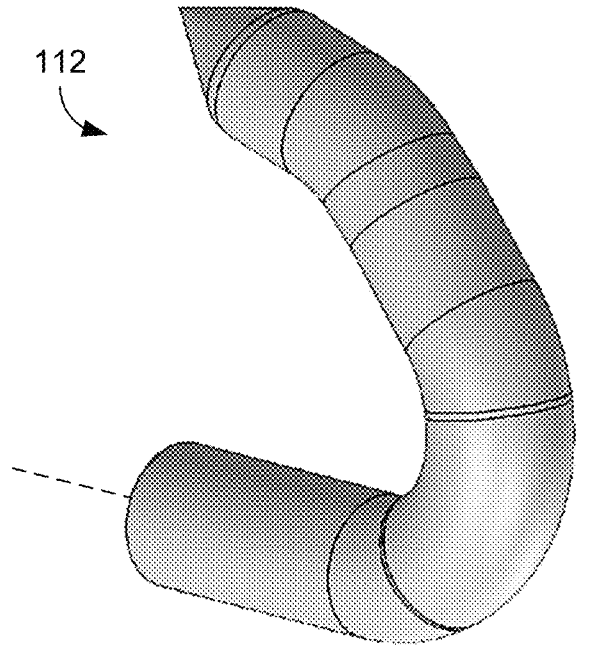
FIGS. 2A and 2B illustrate an example of grips that can be utilized on the electrosurgical device of FIG. 1, in accordance with various embodiments of the present disclosure.
Figure 2B:
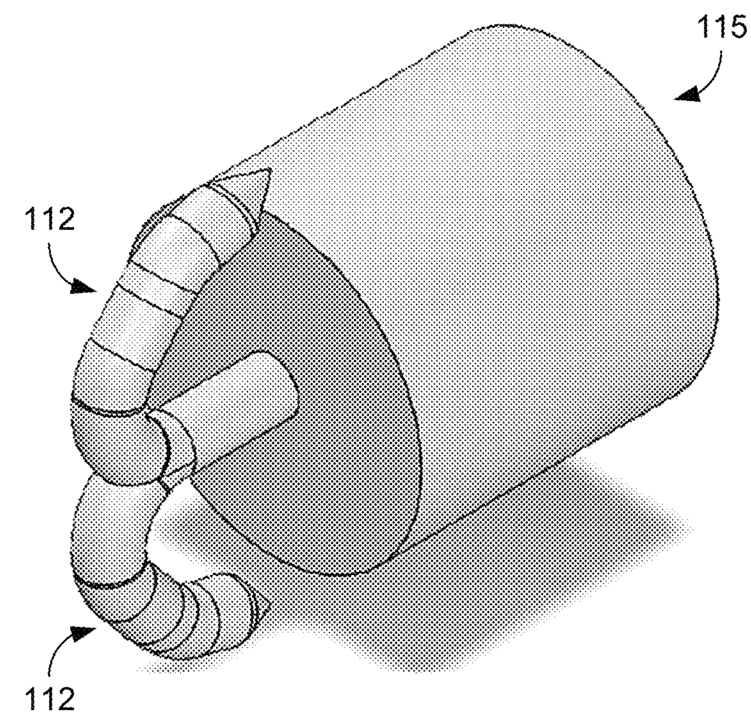
Figure 3:
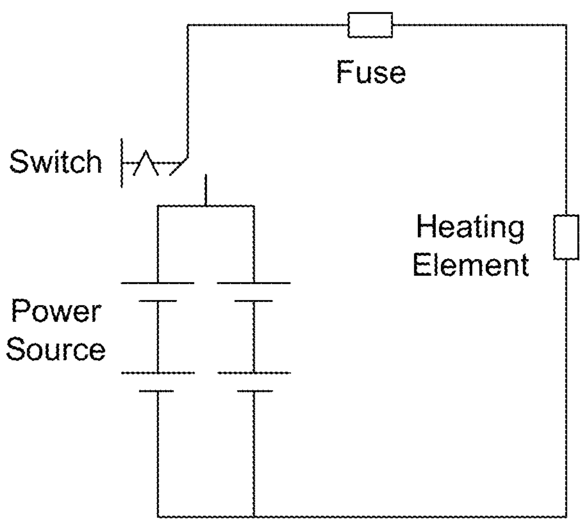
FIG. 3 illustrates an example of heating element control circuitry of the electrosurgical device of FIG. 1, in accordance with various embodiments of the present disclosure.

FIGS. 2A and 2B illustrate an example of grips 112. Each grip 112 can comprise a curved hook that curls from the end of the rod or shaft of the tensioning system 103. As shown in FIG. 2A, the curved hook can curl radially outward from a longitudinal axis of the rod or shaft with the free end of the hook extending back towards the rod or shaft. For example, the free end of the curved hook can curl back in a range from, e.g., about 120 degrees, about 135 degrees, or about 150 degrees to, e.g., about 180 degrees, about 165 degrees or about 150 degrees. In the example of FIG. 2A, the curved hook includes a first bend or bent segment, a first straight segment, a second bend or bent segment and a second straight segment at the final angle. Other combinations of bent and straight segments can be used to from the curved hook of the grip 112. The grips 112 can be fabricated from, e.g., polymer, stainless steel, or other appropriate material. The grips 112 are sized to operate within the incisions of the eye with a hook size of, e.g., about 1 mm each.

In the example of FIG. 1, the tensioning system 103 utilizes two grips 112 to grasp the suture ends. As illustrated in FIG. 2B, the two grips 112 can curl in opposite directions. Other embodiments can include additional grips 112, e.g., equally distributed about the longitudinal axis of the rod or shaft. The grips 112 are attached to a cap 115 that can be coupled or affixed to the end of the rod or shaft. This can offer improved stability for the tensioning system 103. In some implementations, the cap 115 can be detachably attached to the rod or shaft to allow for replacement or substitution of the grips 112.

Extension and retraction of the grips 112 can be controlled by a slider button 118 (or other appropriate switch, wheel or actuator) attached to the rod or shaft connected to the grips 112, which extends into the casing 109 as illustrated in FIG. 1. Suture attachment can be performed using microforceps, a condon snare, or similar device that allows for suture handling. Once the suture ends are affixed to the grips 112, the tensioning system 103 can be activated to twist the suture ends together, thus setting the tension. The tensioning system 103 can comprise a handle 121 coupled to the other end of the rod or shaft, which can extend axially within the casing, opposite the grips 112. The surgeon can rotate the handle 121 at the distal end of the casing 109. As the surgeon rotates the handle 121, the grips 112 also rotate and twist the suture ends together. The tension can be determined by "feel" or visual inspection by the surgeon, or can be sensed (e.g., by sensing torque of the rod or shaft) and indicted by, e.g., a light bar or other indicator on the casing 109. In other embodiments, the rod or shaft can be rotated by, e.g., an electric motor activated by a switch on the casing 109. Tension of the suture may be determined, e.g., using current of the motor.

Once the appropriate tension is reached, the sutures can then be electrocauterized via the heating element of the suture electrocautery system 106. The grips 112 can also be retracted into the casing 103 to perform electrocauterization, e.g., in an insulated chamber to limit heat diffusion to the rest of the device 100 and immediate eye surroundings. Each grip 112 can grasp a suture end and pull the suture ends toward or into the device 100 via the slider button 118 on the side of the casing 109. Retracting the tensioning system 103 can bring the suture ends towards a heating element of the suture electrocautery system 106 mounted or attached to the device 100. The heating element can then be activated (e.g., by a control switch or button 124 on the casing 109) to thermally ligate the suture ends. This makes it both easier to electrocauterize the sutures, as the ends are already brought together, as well as help set the suture tension which the surgeon would determine based on visual inspection.

The heating element of the suture electrocautery system 106 can be powered by a power source such as, e.g., one or more battery, which can be sized for a single or multiple electrocauterizing events. In a nonlimiting example, the heating element can comprise a fine filament tip, which can heat to the temperature needed to cauterize the suture almost instantaneously after activation. For example, the heating element can be a small length of Kanthal resistance wire (which can be formed into a coil) or other appropriate resistive component. The fine filament tip can be connected to internal wiring powered by a power source (e.g., a battery) contained within the casing 109.

Once the sutures are twisted and retracted into (or adjacent to) an insulated chamber at the proximal end of the casing 109, the suture ends are near the heating element. The heating element of the suture electrocautery system 106 can be mounted in the casing 109 as illustrated in FIG. 1 or can extend out of the casing 109. Once the tension is set, the heating element can be activated to bond the suture ends together via electrocauterization. When the battery's voltage is applied to the wire, the wire heats up to a sufficient temperature to melt the suture ends to form a bond. For example, approximately 4.5 Volts applied at 2 Amps can provide the heat needed to melt a polypropylene suture on the order of a few seconds. Other voltage and current combinations can be used to provide the heating needed to electrocauterize the suture. The slider button 118 can then be moved in the opposite direction to extend the rod or shaft and push the now joined suture out of or away from the device 100. The joined suture can be correctly oriented in the Schlemm's canal by the surgeon.

The casing 109 can be sized and configured to single-hand operation. In a nonlimiting example, the casing 109 can be a simple plastic casing or can be made of other appropriate material suitable for the surgical environment. The casing 109 can include a proximal opening at the end of an insulated chamber where the grips 112 on the rod or shaft can protrude. The casing 109 can include a distal opening for the handle 121 or a knob to couple to the rod or shaft to control suture twist and tensioning. In some implementations, a releasable ratchet mechanism can be included to maintain tension on the sutures during electrocauterization. A control switch or button 124 can be located on the side or distal end of the casing 109 for heating element activation.

In some embodiments, the electrosurgical device 100 can safely utilize thermal cautery to attach two ends of suture with an adjustable tension within the anterior chamber of the eye (ab interno). This is an alternative to the traditional Siepser knot where sutures must be externalized, knotted ab externo and subsequently pulled or "thrown" into the anterior chamber. The Siepser technique works well for suturing iris, but is time consuming, technically challenging and not conducive to knotting in the angle of the eye where specialized lenses (gonioscopy lenses) are needed to visualize the tissue.

As previously discussed, the electrosurgical device 100 can be used to grab, internalize and thermally heat a polypropylene suture together at a desired tension. The device 100 can be used for ab interno canaloplasty glaucoma surgery, for which the suture is first advanced through Schlemm's canal. The tension on the suture can be created by the device 100 and then maintained by the thermal "knot". This suture can be left in the eye to maintain inward tension on the trabecular meshwork, and thus dilate Schlemm's canal. The dilation of the Schlemm's canal can improve aqueous outflow from the eye, thus reducing intraocular pressure in the treatment of glaucoma. The device 100 can also be used for suturing the iris during a pupilloplasty procedure.

In various embodiments, a 2.0 to 2.6 mm temporal main wound can be created in the cornea with a keratome to start the surgery. A viscoelastic substance can be used to maintain the anterior chamber and provide to act as a coupling agent on the surface of the cornea. Per usual ab interno glaucoma angle surgery or minimally invasive glaucoma surgery (MIGS), a gonioscopy lens is placed on the cornea and held on the eye with the surgeon's non-dominate hand. This lens provides a direct view to the nasal trabecular meshwork. A 10-0 or 9-0 polypropylene suture can be advanced 360 degrees around Schlemm's canal via a standard nasal goniotomy incision through the trabecular meshwork in which access to Schlemm's canal can be obtained using, e.g., a 25 to 27 gauge needle, MVR blade, Sinskey hook, or other alternative.

Once both ends of the suture are visualized exiting the goniotomy incision, the electrosurgical device 100 can be inserted through the keratome wound. The grips 112 of the device 100 can then be used to grab or hook both ends of the suture. The grips 112 can be retracted to internalize the ends of the tensioned suture into an insulated chamber within the casing 109. The handle 121 of the device 100 can be used to control tension of the suture by rotating the grips 112, providing the surgeon the ability to control tension with one hand. The device 100 can allow for retraction of the suture ends and grips 112 using, e.g., the slider button 118. The twisting of the suture ends both creates tension on the suture to dilate Schlemm's canal and brings both ends of the suture within proximity permitting thermal adhesion to one another.

Once the correct tension is achieved (which can be indicated by inward tenting of the trabecular meshwork), the heating element can be activated by the surgeon (or by a surgical assistant) to adhere the suture ends together. Following suture end adhesion, the suture can be released from the device 100, the device 100 removed, and micro-scissors used to cut any excess suture. The gonioscopy lens can be removed from the eye and viscoelastic irrigated out of the anterior chamber. The main wound can then be hydrated, checked for leakage, and the patient's eye shielded at completion of the surgery.

Figure 4A:
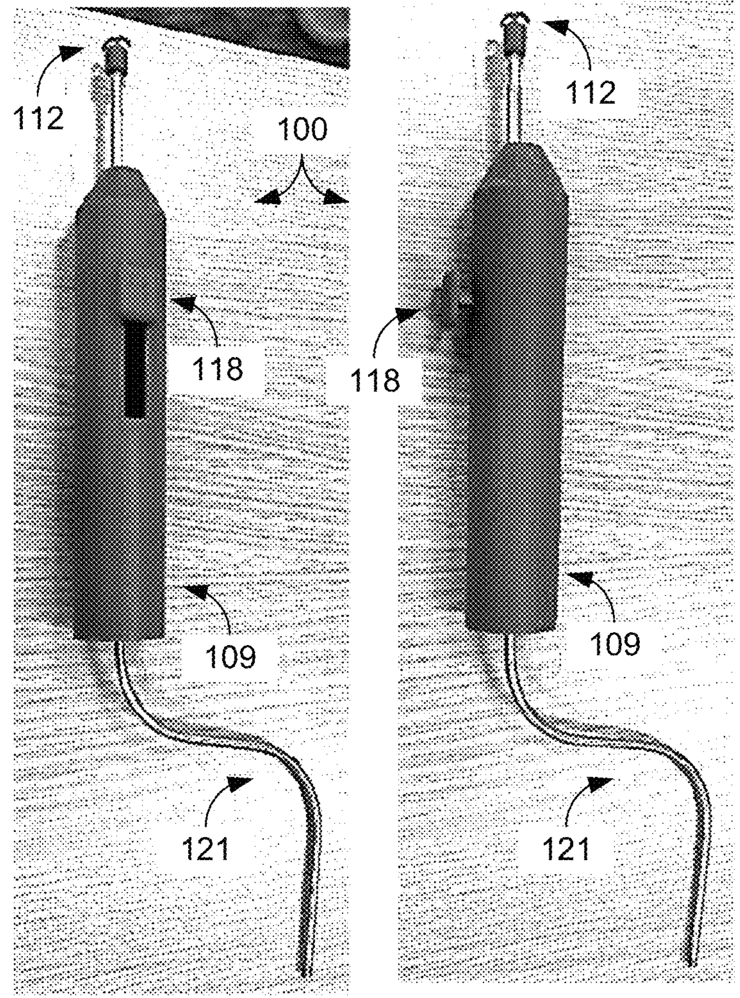
FIGS. 4A-4D are images showing an implemented prototype of an example of the electrosurgical device of FIG. 1, in accordance with various embodiments of the present disclosure.
Figure 4B:
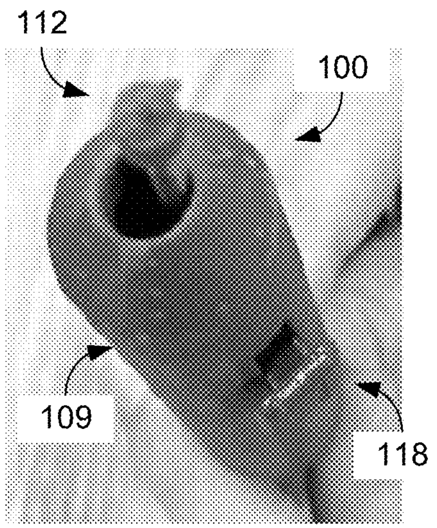
Figure 4C:
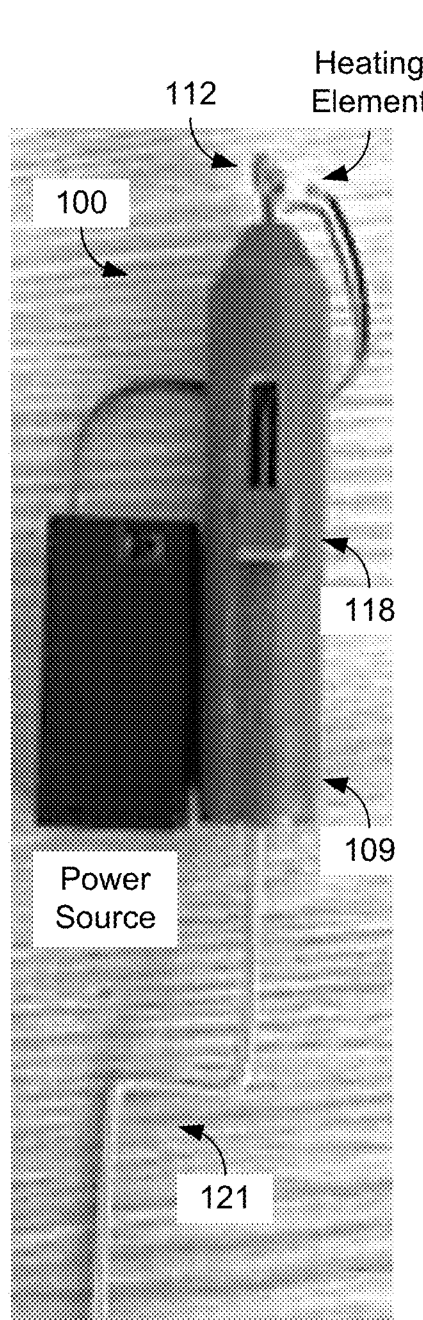

Prototypes of an electrosurgical device 100 was implemented for proof of concept. FIGS. 4A-4D are images illustrating the fabricated device 100. The images of FIG. 4A shows the fabricated device 100, which includes grips 112 (two curved hooks) to snare the ends of a suture, an external slider button 118 to extend and retract the grips 112, and a handle 121 at the end of the rod or shaft (e.g., stainless steel) coupled to the grips 112. The rod or shaft can extend through an outer shaft (e.g., stainless steel tube) to allow for movement within the casing 109. The image of FIG. 4B shows the rod or shaft coupled to the grips 112 extending through the opening on the proximal end of the casing 109. The initial prototypes were implemented with the power source separate from the casing 109, with the heating element positioned to work in conjunction with the main body. The image of FIG. 4C illustrates the heating element positioned adjacent to the grips 112 of the device 100 and connected to a battery as the power source. A control switch can be used to activate the heating element.

Figure 4D:
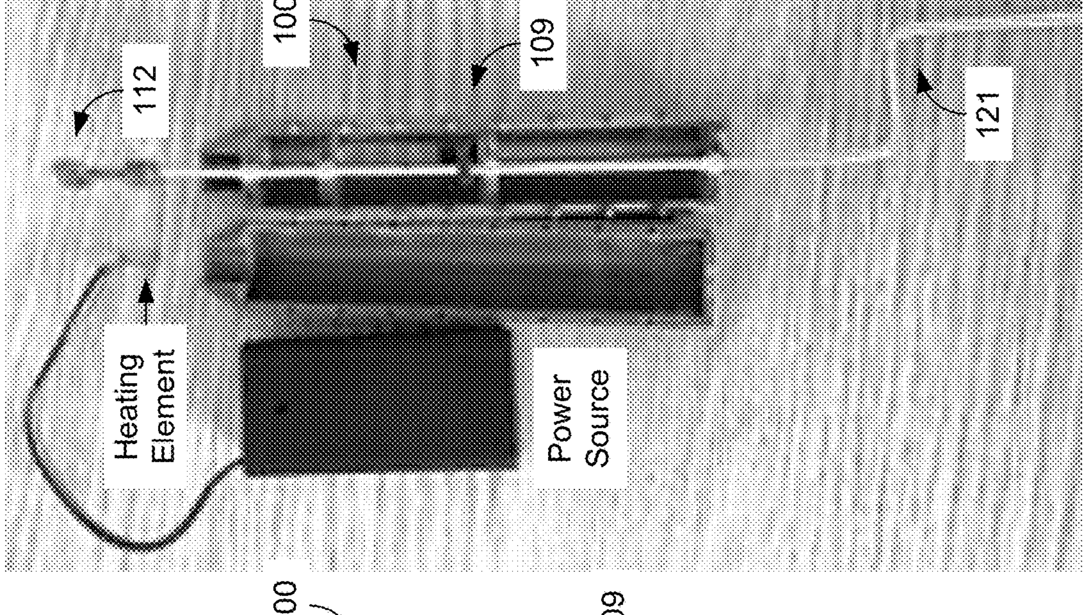
Figure 4D:
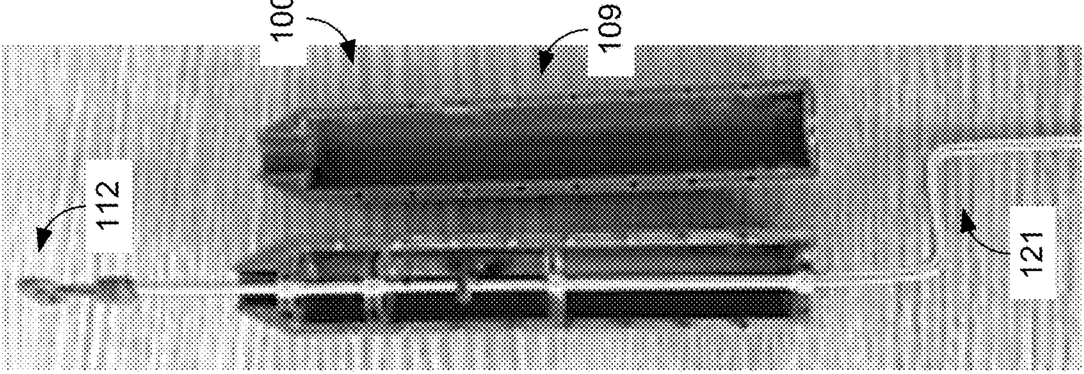
Figure 4D:
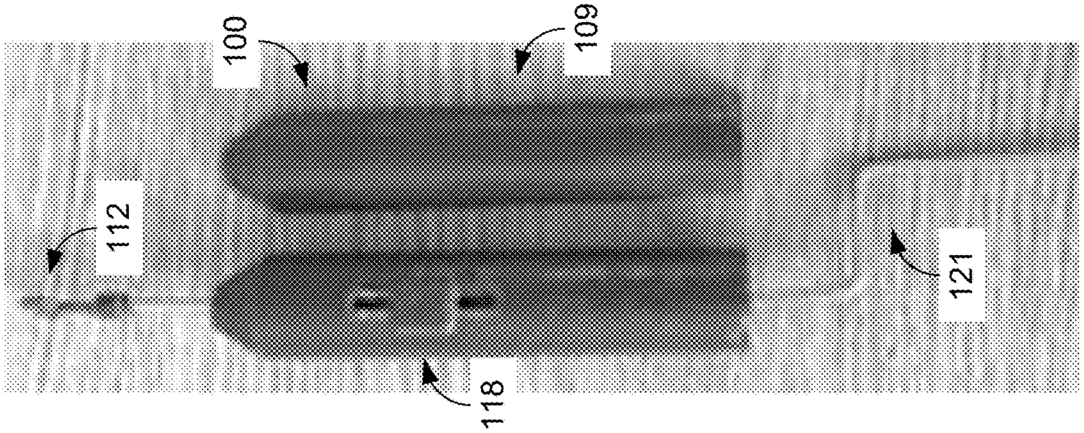

The images of FIG. 4D show the device 100 with the casing split open to view the exterior and interior features of the fabricated device 100. The split casing 109 can ease fabrication of the device 100. As shown in FIG. 4D, support disks (e.g., polymer) can be positioned at various locations along the casing 109 to support and stabilize the rod or shaft coupled to the grips 112 extends. In some embodiments, an outer shaft (or tube) can be included to facilitate movement of the rod or shaft in the casing 109.

Figure 5A:
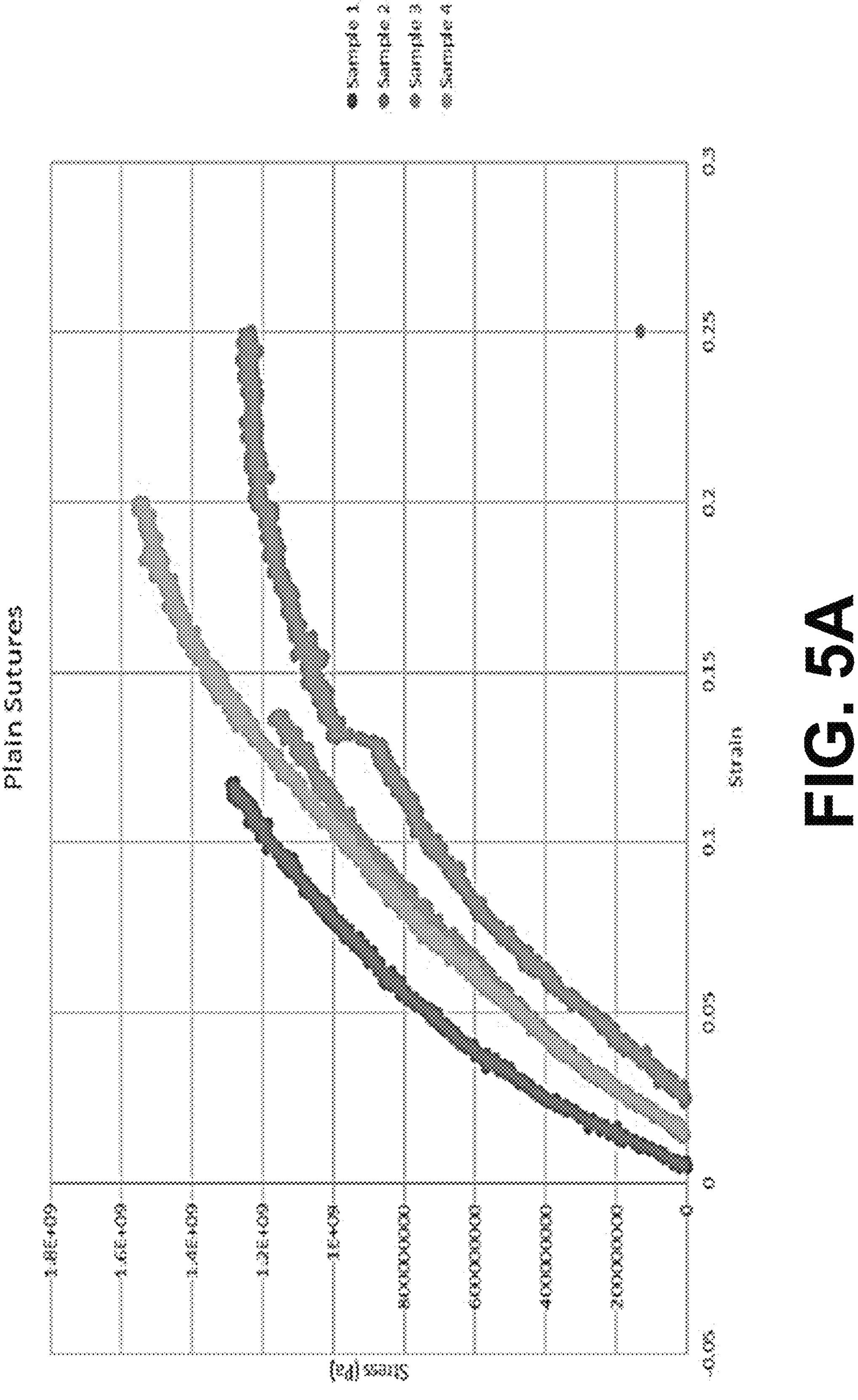
FIGS. 5A-5C illustrate examples of suture testing results, in accordance with various embodiments of the present disclosure.
Figure 5B:
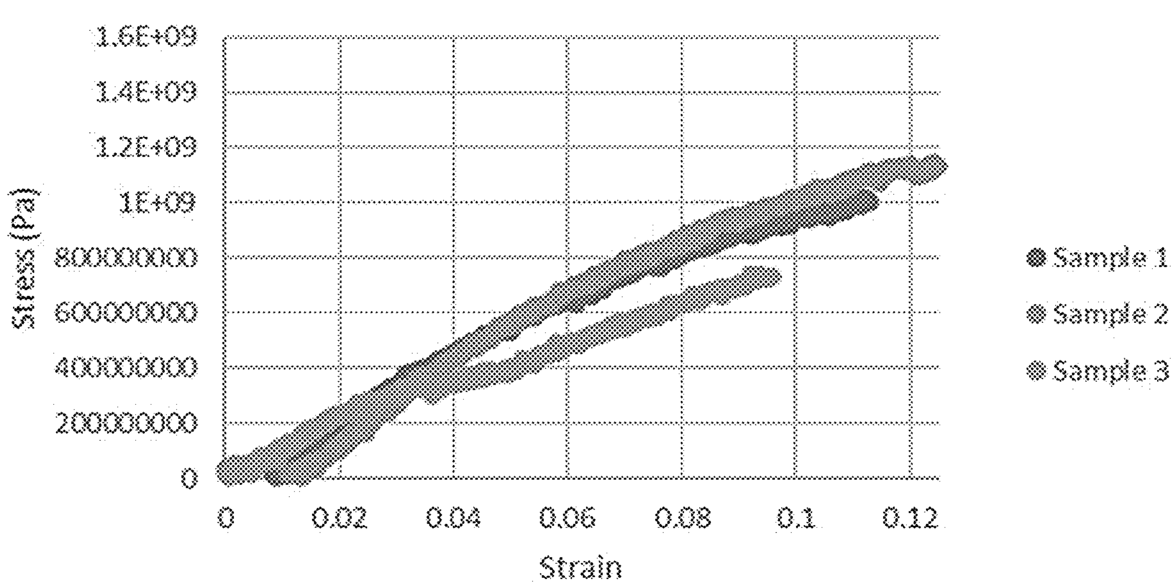
Figure 5C:
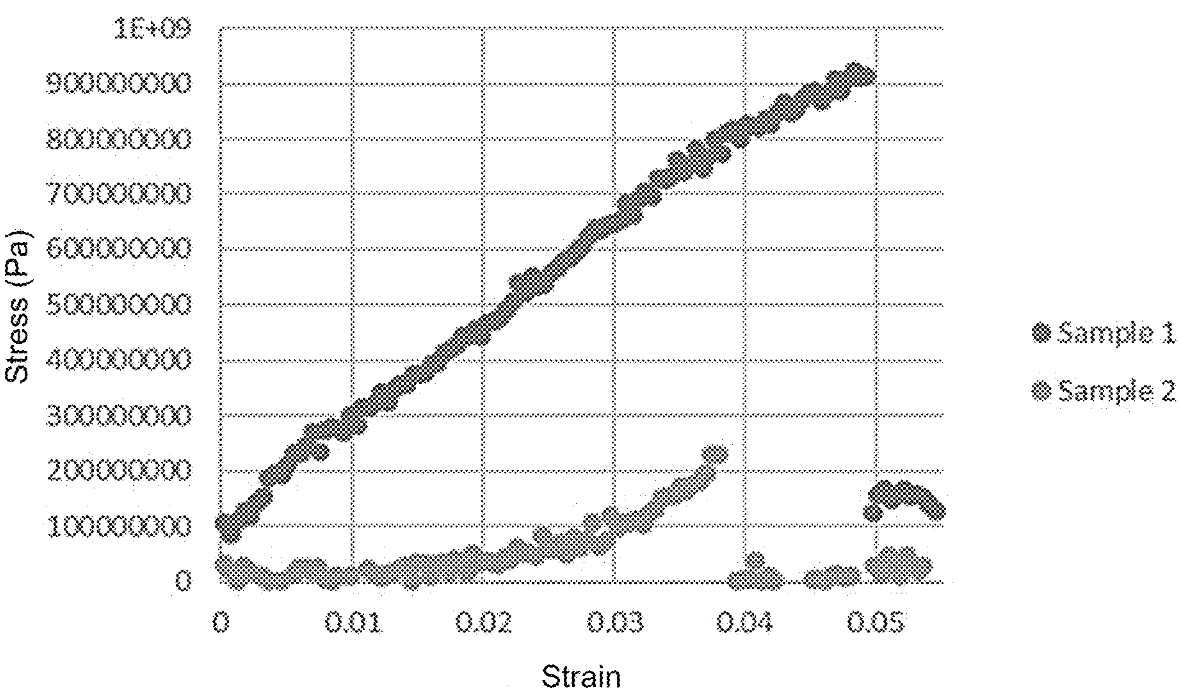

Results of the initial testing of the electrosurgical device 100 are shown in FIGS. 5A-5C. FIG. 5A illustrates an example of the stress/strain curve for plain suture samples. It was found that an average stress of 1.3 GPa was needed to break the plain sutures. FIG. 5B shows an example of the stress/strain curve for knotted suture samples. It was found that an average stress of 1.0 GPa was needed to break the knotted sutures. FIG. 5C shows an example of the stress/strain curve for electrocauterized suture samples. It was found that an average stress of 0.57 GPa was needed to break the electrocauterized sutures. The use of both knots and electrocautery is sufficient for tensioning, as they both failed well above 128 kPa, which is the tension within the eye's trabecular meshwork.

Figures 6A, 6B:
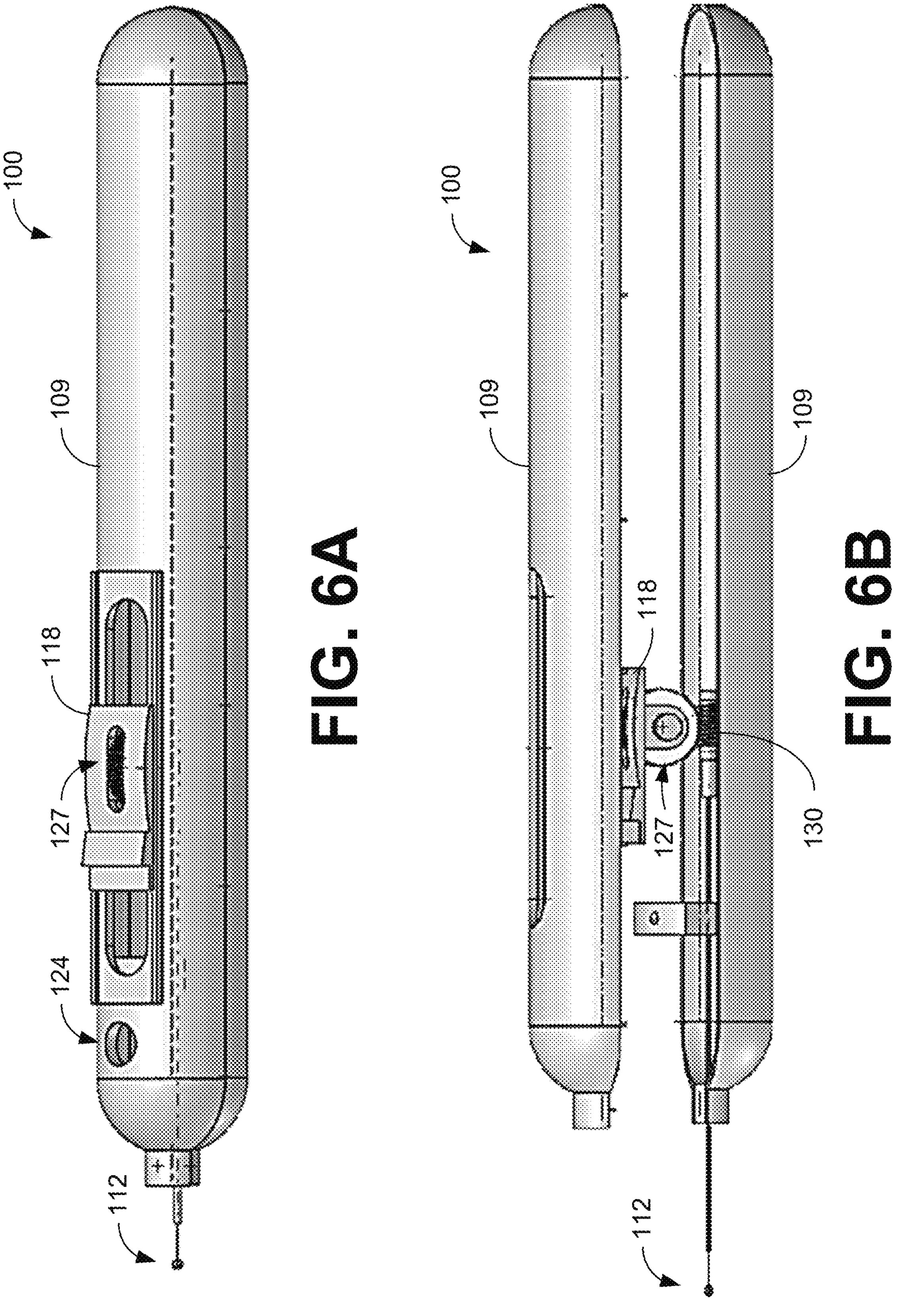
FIGS. 6A-6B and 7A-7C illustrate other examples of an electrosurgical device that can be used for suture tensioning and electrocautery, in accordance with various embodiments of the present disclosure.

Referring now to FIGS. 6A and 6B, shown is another example of an electrosurgical device 100. In this example, the tensioning system 103 is configured to rotate the grips 112 using a wheel gear 127 integrated into the slider button 118 instead of a handle 121 as shown in FIG. 1. As illustrated in FIG. 6B, the wheel gear 127 can include a gear that engages with a worm gear 130 affixed to the rod or shaft attached to the grips 112. By rotating the wheel gear 127, the worm gear 130 is rotated causing the grips 112 to rotate thereby tying the attached suture ends. The slider button 118 can be engaged with the rod or shaft to allow for extension or retraction of the grips 112 by moving along a slider track. In this configuration, the rod or shaft extends into the casing 109 from the proximal end to the worm gear 130 but does not need to extend through the casing 109 to the distal end. Supports can be included in the casing 109 to ensure stability of the slider button 118, wheel gear 127, worm gear 130, and/or rod or shaft attached to the grips 112. The control switch or button 124 can be located adjacent to the slider track of the slider button 118 for activation of the heating element for electrocauterization of the suture. The slider button 118 can retract the grips 112 into the insulated chamber, adjacent to the heating element, located at the proximal end of the device 100.

Figures 7A, 7B, 7C:
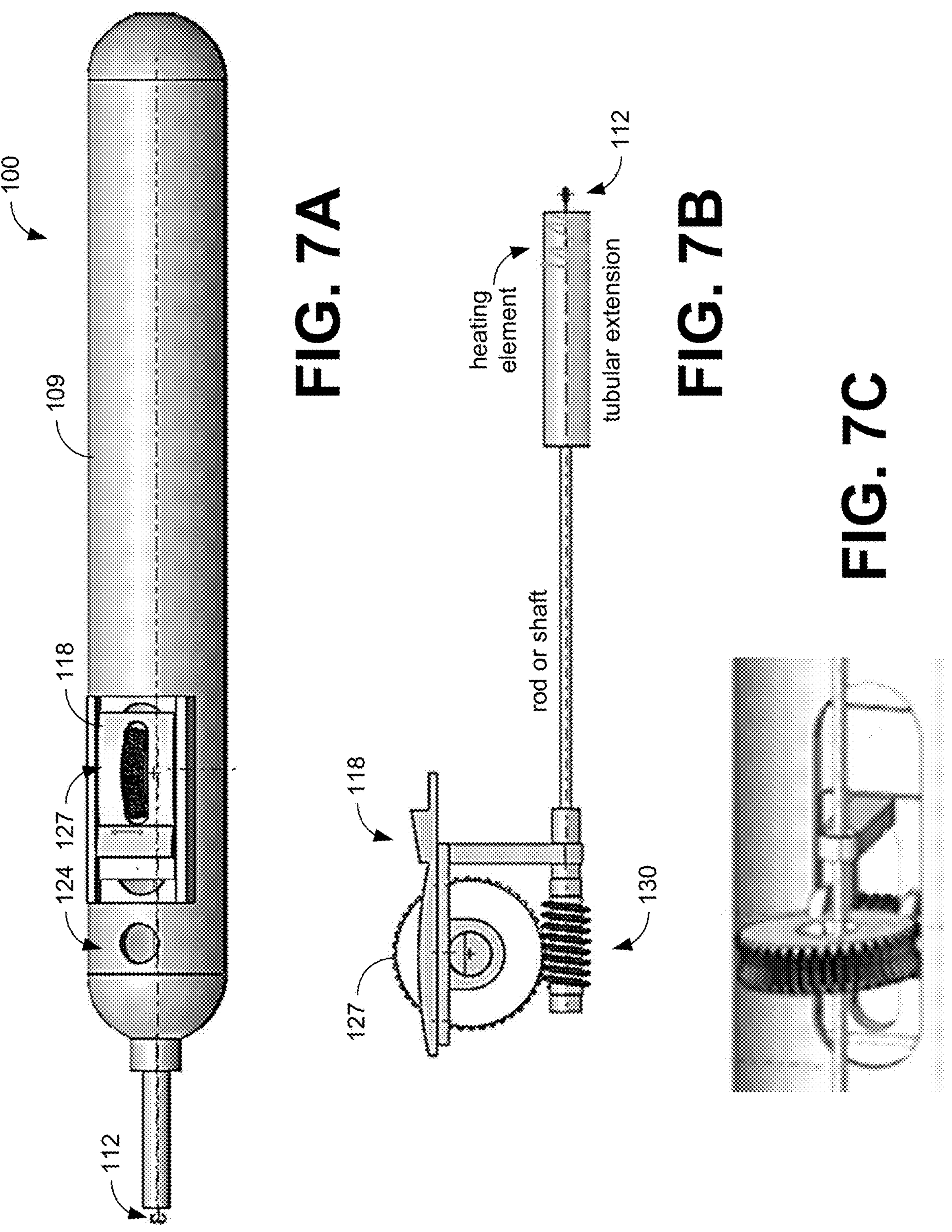

FIG. 7A illustrates another example of an electrosurgical device 100. In this example, a tubular extension of the casing 109 has been added to the proximal end of the casing 109 that allows the heating element to be located closer to the grips 112. FIG. 7B shows the engagement of the wheel gear 127 with the worm gear 130 affixed to the rod or shaft extending through the tubular extension and attached to the grips 112. By locating the heating element at the proximal end of the tubular extension, the movement needed to place the tied suture adjacent to the heating element for binding is reduced. For example, the tubular extension can have a length of about 14 mm and a diameter of about 2 mm, which can allow a 5 mm movement distance of the slider button 118 to position the grips 112 adjacent to the heating element.

The tubular extension also provides protection from the heating element. The location of the heating element allows the movement distance of the slider button 118 along the slider track to be reduced as shown.

By rotating the wheel gear 127 in FIG. 7B, the worm gear 130 is rotated causing the grips 112 to rotate thereby tying the attached suture ends. The slider button 118 can be engaged with the rod or shaft to allow for extension or retraction of the grips 112 by moving along the slider track. In this configuration, movement of the slider button 118 can retract the grips 112 toward the heating element where the ends of the suture can be melted together. In other embodiments, a wheel gear can be affixed to the rod or shaft and a worm gear can be incorporated into the slider button 118 as shown in FIG. 7C. This arrangement can provide finer control of the rotation of the grips 112 and tension of the suture.

Locating the heating element at the proximal end of the tubular extension can also provide additional space in the casing 109 for a power source. The additional space can also facilitate incorporation of a motor for rotation of the grips 112. The motor can replace the wheel gear and worm gear for rotation of the grips 112. Activation of the motor can be controlled using one or more switch or button located on the casing 109 or on the slider button 118. The rod or shaft can be configured to engage with the motor shaft allowing for axial movement of the rod or shaft over or through the motor shaft.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A suture tensioning and electrocautery device to perform ab interno canaloplasty or pupilloplasty surgery, comprising:

a casing having a proximal end and a distal end;

suture grips protruding out of the proximal end of the casing;

a suture tensioning and retracting system connected to the suture grips; and a suture electrocautery system;

wherein the suture tensioning and retracting system comprises a proximal end, a distal end, an outer shaft, and an inner shaft; wherein the outer shaft is adjustable to allow axial translation of the suture grips to protrude or retract away from the proximal end of the casing; wherein the inner shaft is adjustable to allow for axial rotation of the suture grips to twist suture ends of a suture together and produce tension in the suture.

2. The device of claim 1, wherein the suture grips are coupled to the inner shaft at the proximal end of the suture tensioning and retracting system.

3. The device of claim 2, wherein a manual handle or knob is coupled to the distal end of the suture tensioning and retracting system to control tension of the suture with one hand.

4. The device of claim 1, wherein the suture electrocautery system comprises a switch, a power source, and a heating element.

5. The device of claim 4, wherein the heating element is a resistance wire.

6. The device of claim 4, wherein the power source is a battery.

7. The device of claim 4, wherein the suture electrocautery system is configured to produce sufficient heat to melt a 10-0 or 9-0 polypropylene suture or a nylon suture.

8. The device of claim 7, wherein the power source is sized for a single use operation.

9. The device of claim 1, wherein the casing contains an insulated chamber at its proximal end.

10. The device of claim 9, wherein the suture electrocautery system comprises a heating element positioned in the insulated chamber.

11. The device of claim 10, wherein the suture grips are located adjacent to the heating element when retracted into the insulated chamber.

12. A suture tensioning and electrocautery device to perform ab interno canaloplasty or pupilloplasty surgery, comprising:

a casing having a proximal end and a distal end;

suture grips protruding out of the proximal end of the casing;

a suture tensioning and retracting system connected to the suture grips; and a suture electrocautery system;

wherein the suture grips comprise first and second grips having curved hooks configured to attach to ends of a suture, wherein rotation of the suture grips twist the suture ends together and produce tension in the suture.

13. A method to perform ab interno canaloplasty using the suture tensioning and electrocautery device of claim 1, comprising:

advancing a suture through a first incision on the cornea of an eye and through a second incision within the eye through Schlemm's canal opposite the first incision, thereby exposing first and second ends of the suture at the second incision;

affixing the first and second ends of the suture to the suture grips protruding out of a proximal end of the suture tensioning and electrocautery device;

tying the first and second ends of the suture and tensioning the suture by rotating the suture grips to dilate the Schlemm's canal; and heating the tied first and second ends of the suture to adhere the first and second ends together and maintain the tensioning of the suture thereby sustaining dilation of the Schlemm's canal.

14. The method of claim 13, wherein the tied first and second ends of the suture are heated inside an insulated chamber located at the proximal end of the suture tensioning and electrocautery device.

15. The method of claim 14, wherein the tied first and second ends of the suture are heated by a heating element in the insulated chamber.

16. The method of claim 15, wherein the heating element is a resistance wire.

17. The method of claim 13, wherein the suture grips comprise first and second grips having curved hooks configured to attach to ends of the suture, wherein rotation of the suture grips twist the suture ends together and produce tension in the suture.

18. The method of claim 17, wherein the suture comprises a 10-0 or 9-0 polypropylene suture or a nylon suture.

19. The method of claim 13, comprising creating the first incision on the cornea of the eye and creating the second incision within the eye.

* * * * *